(12) United States Patent
Rosenbluth et al.

(10) Patent No.: US 8,784,434 B2
(45) Date of Patent: Jul. 22, 2014

(54) METHODS AND APPARATUS FOR TREATING EMBOLISM

(71) Applicant: Inceptus Medical LLC, Aliso Viejo, CA (US)

(72) Inventors: Robert F. Rosenbluth, Laguna Niguel, CA (US); Brian J. Cox, Laguna Niguel, CA (US); Paul Lubock, Monarch Beach, CA (US)

(73) Assignee: Inceptus Medical, Inc., Aliso Viejo, CA (US)

( * ) Notice: Subject to any disclaimer, the term of this patent is extended or adjusted under 35 U.S.C. 154(b) by 0 days.

(21) Appl. No.: 13/843,742

(22) Filed: Mar. 15, 2013

(65) Prior Publication Data

US 2014/0155908 A1    Jun. 5, 2014

Related U.S. Application Data

(60) Provisional application No. 61/728,775, filed on Nov. 20, 2012, provisional application No. 61/750,277, filed on Jan. 8, 2013.

(51) Int. Cl.
*A61B 17/22* (2006.01)

(52) U.S. Cl.
USPC .......................................................... 606/127

(58) Field of Classification Search
USPC ......... 606/127, 128, 159, 191, 192, 194, 195, 606/198, 200
See application file for complete search history.

(56) References Cited

U.S. PATENT DOCUMENTS

| | | | |
|---|---|---|---|
| 3,435,826 | A | 4/1969 | Fogarty |
| 3,613,664 | A | 10/1971 | Willson et al. |
| 3,923,065 | A | 12/1975 | Nozick et al. |
| 4,030,503 | A | 6/1977 | Clark, III |
| 4,650,466 | A | 3/1987 | Luther |
| 4,873,978 | A | 10/1989 | Ginsburg |
| 4,921,484 | A | 5/1990 | Hillstead |
| 4,936,312 | A | 6/1990 | Tsukagoshi |
| 5,009,659 | A | 4/1991 | Hamlin et al. |
| 5,011,488 | A | 4/1991 | Ginsburg |
| 5,059,178 | A | 10/1991 | Ya |
| 5,102,415 | A | 4/1992 | Guenther et al. |

(Continued)

FOREIGN PATENT DOCUMENTS

| | | |
|---|---|---|
| JP | 06-190049 A | 7/1994 |
| JP | 6190049 | 7/1994 |

(Continued)

OTHER PUBLICATIONS

Verma, R., MD et al., "Evaluation of a Newly Developed Percutaneous Thrombectomy Basket Device in Sheep With Central Pulmonary Embolisms", *Investigative Radiology*, Oct. 2006; 41: 729-734, Lippincott Williams & Wilkins.

(Continued)

*Primary Examiner* — Ryan Severson
*Assistant Examiner* — Jonathan W Miles
(74) *Attorney, Agent, or Firm* — Perkins Coie LLP

(57) ABSTRACT

A method and apparatus for treating a clot in the blood vessel of a patient, and particularly the treatment of a pulmonary embolism is disclosed. The treatment includes restoring flow through the clot followed by clot removal, either partially or substantially completely. The clot treatment device is expandable into the blood vessel and may contain radial extensions that assist in restoring flow as well as in removing clot material.

30 Claims, 9 Drawing Sheets

(56) References Cited

U.S. PATENT DOCUMENTS

| | | |
|---|---|---|
| 5,192,286 A | 3/1993 | Phan et al. |
| 5,192,290 A | 3/1993 | Hilal |
| 5,370,653 A | 12/1994 | Cragg |
| 5,476,450 A | 12/1995 | Ruggio |
| 5,490,859 A | 2/1996 | Mische et al. |
| 5,681,335 A | 10/1997 | Serra et al. |
| 5,746,758 A | 5/1998 | Nordgren et al. |
| 5,827,304 A | 10/1998 | Hart |
| 5,895,400 A | 4/1999 | Abela |
| 5,902,263 A | 5/1999 | Patterson et al. |
| 5,972,019 A | 10/1999 | Engelson et al. |
| 6,027,520 A | 2/2000 | Tsugita et al. |
| 6,030,397 A | 2/2000 | Monetti et al. |
| 6,066,149 A | 5/2000 | Samson et al. |
| 6,146,396 A | 11/2000 | Kónya et al. |
| 6,221,006 B1 | 4/2001 | Dubrul et al. |
| 6,238,412 B1 | 5/2001 | Dubrul et al. |
| 6,383,205 B1 | 5/2002 | Samson et al. |
| 6,454,775 B1 | 9/2002 | Demarais et al. |
| 6,458,139 B1 | 10/2002 | Palmer et al. |
| 6,514,273 B1 | 2/2003 | Voss et al. |
| 6,544,279 B1 | 4/2003 | Hopkins et al. |
| 6,605,102 B1 | 8/2003 | Mazzocchi et al. |
| 6,635,070 B2 | 10/2003 | Leeflang et al. |
| 6,685,722 B1 | 2/2004 | Rosenbluth et al. |
| 6,692,504 B2 | 2/2004 | Kurz et al. |
| 6,699,260 B2 | 3/2004 | Dubrul et al. |
| 6,767,353 B1 | 7/2004 | Shiber |
| 7,004,954 B1 | 2/2006 | Voss et al. |
| 7,008,434 B2 | 3/2006 | Kurz et al. |
| 7,052,500 B2 | 5/2006 | Bashiri et al. |
| 7,179,273 B1 | 2/2007 | Palmer et al. |
| 7,244,243 B2 | 7/2007 | Lary |
| 7,320,698 B2 | 1/2008 | Eskuri |
| 7,578,830 B2 | 8/2009 | Kusleika et al. |
| 7,938,820 B2 | 5/2011 | Webster et al. |
| 7,993,302 B2 | 8/2011 | Hebert et al. |
| 7,993,363 B2 | 8/2011 | Demond et al. |
| 8,043,313 B2 | 10/2011 | Krolik et al. |
| 8,052,640 B2 | 11/2011 | Fiorella et al. |
| 8,057,496 B2 | 11/2011 | Fischer, Jr. |
| 8,066,757 B2 | 11/2011 | Ferrera et al. |
| 8,070,791 B2 | 12/2011 | Ferrera et al. |
| 8,075,510 B2 | 12/2011 | Aklog et al. |
| 8,100,935 B2 | 1/2012 | Rosenbluth et al. |
| 8,118,829 B2 | 2/2012 | Carrison et al. |
| 8,246,641 B2 | 8/2012 | Osborne et al. |
| 8,303,612 B2 | 11/2012 | Nakao et al. |
| 8,480,697 B2 | 7/2013 | Kucharczyk et al. |
| 2007/0255252 A1 | 11/2007 | Mehta |
| 2008/0167678 A1 | 7/2008 | Morsi |
| 2008/0269798 A1 | 10/2008 | Ramzipoor et al. |
| 2009/0054918 A1 | 2/2009 | Henson |
| 2009/0163846 A1 | 6/2009 | Aklog et al. |
| 2009/0182362 A1 | 7/2009 | Thompson et al. |
| 2009/0248059 A1 | 10/2009 | Morsi |
| 2010/0114113 A1 | 5/2010 | Dubrul et al. |
| 2010/0318178 A1 | 12/2010 | Rapaport et al. |
| 2011/0060212 A1 | 3/2011 | Slee et al. |
| 2011/0152920 A1 | 6/2011 | Eckhouse et al. |
| 2011/0152993 A1 | 6/2011 | Marchand et al. |
| 2011/0190806 A1 | 8/2011 | Wittens |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2012/0101510 A1 | 4/2012 | Lenker et al. |
| 2012/0143239 A1 | 6/2012 | Aklog et al. |
| 2012/0165919 A1 | 6/2012 | Cox et al. |
| 2012/0179181 A1 | 7/2012 | Straub et al. |
| 2012/0271231 A1 | 10/2012 | Agrawal |

FOREIGN PATENT DOCUMENTS

| | | |
|---|---|---|
| JP | 2004-097807 A | 4/2004 |
| JP | 2005-230132 A | 9/2005 |
| JP | 2005-323702 A | 11/2005 |
| JP | 2006-094876 A | 4/2006 |
| WO | WO 97/17889 A1 | 5/1997 |
| WO | WO-2005046736 | 5/2005 |
| WO | WO-2006110186 | 10/2006 |
| WO | WO 2007/092820 A2 | 8/2007 |
| WO | WO 2009/155571 A1 | 12/2009 |
| WO | WO 2010/010545 A1 | 1/2010 |
| WO | WO 2010/023671 A2 | 3/2010 |
| WO | WO 2010/049121 A2 | 5/2010 |
| WO | WO 2010/102307 A1 | 9/2010 |
| WO | WO 2011/054531 A2 | 5/2011 |
| WO | WO 2012/009675 A2 | 1/2012 |
| WO | WO 2012/065748 A1 | 5/2012 |

OTHER PUBLICATIONS

Konstantinides, S. et al., "Pulmonary embolism hotline 2012—Recent and expected trials", *Thrombosis and Haemostasis*, Jan. 9, 2013:33; 43-50, Center for Thrombosis and Haemostasis, Johannes Gutenberg University Medical Center, Mainz, Germany.

Konstantinides, S. et al., "Pulmonary embolism: risk assessment and management", *European Society of Cardiology; European Heart Journal*, Sep. 7, 2012:33, 3014-3022, Center for Thrombosis and Haemostasis, Johannes Gutenberg University Medical Center, Mainz, Germany.

Kuo, W. MD, "Endovascular Therapy for Acute Pulmonary Embolism", Continuing Medical Education Society of Interventional Radiology ("CME"); *Journal of Vascular and Interventional Radiology*, Feb. 2012: 23:167-179, Stanford University Medical Center, Stanford, CA, USA.

Liu, S. et al, "Massive Pulmonary Embolism: Treatment with the Rotarex Thrombectomy System", *Cardiovascular Interventional Radiology*; 2011: 34:106-113, Springer Science and Business Media, LLC and the Cardiovascular and Interventional Radiological Society of Europe.

Lee, L. et al, "Massive pulmonary embolism: review of management strategies with a focus on catheter-based techniques", *Expert Rev. Cardiovasc. Ther*. 8(6), 863-873 (2010).

Kuo, W. et al., "Catheter-directed Therapy for the Treatment of Massive Pulmonary Embolism: Systematic Review and Meta-analysis of Modern Techniques", *Journal of Vascular and Interventional Radiology*, Nov. 2009: 20:1431-1440, Stanford University Medical Center, Stanford, CA, USA.

Goldhaber, S., "Advanced treatment strategies for acute pulmonary embolism, including thrombolysis and embolectomy", *Journal of Thrombosis and Haemostasis*, 2009: 7 (Suppl. 1): 322-327, Cardiovascular Division, Department of Medicine, Brigham and Women's Hospital, Harvard Medical School, Boston, MA, USA.

Gupta, S. et al., "Acute Pulmonary Embolism Advances in Treatment", *JAPI, Association of Physicians India*, Mar. 2008, vol. 56, 185-191, Consultant Interventional Cardiologist, SDM Hospital, Jaipur, India; Consultant and Former Professor and Head of Dept. of Medicine, Armed Forces Medical College, Pune, India.

Tapson, V., "Acute Pulmonary Embolism", *The New England Journal of Medicine*, Mar. 6, 2008:358:2037-52, Massachusetts Medical Society, MA, USA.

Kuo, W. et al., "Catheter-Directed Embolectomy, Fragmentation, and Thrombolysis for the Treatment of Massive Pulmonary Embolism After Failure of Systemic Thrombolysis", *American College of CHEST Physicians 2008*: 134:250-254, Northbrook, IL, USA.

Goldhaber, S. et al. "Percutaneous Mechanical Thrombectomy for Acute Pulmonary Embolism—A Double-Edged Sword", *American College of CHEST Physicians*, Aug. 2007:132:2, 363-372, Northbrook, IL, USA.

Kucher, N., "Catheter Interventions in Massive Pulmonary Embolism", *CardiologyRounds*, Mar. 2006 vol. 10, Issue 3; Cardiovascular Division of Brigham and Women's Hospital, Boston, MA, USA.

(56) References Cited

OTHER PUBLICATIONS

Kucher, N. et al., "Management of Massive Pulmonary Embolism", *Radiology*, Sep. 2005:236:3 852-858; Cardiovascular Division of Brigham and Women's Hospital, Boston, MA, USA.

Kucher, N. et al., "Percutaneous Catheter Thrombectomy Device for Acute Pulmonary Embolism: In Vitro and in Vivo Testing", *Circulation*, Sep. 2005:112:e28-e32; American Heart Association, Dallas, TX, USA.

Reekers, J. et al., "Mechanical Thrombectomy for Early Treatment of Massive Pulmonary Embolism", *CardioVascular and Interventional Radiology*, 2003:26:246-250, Springer-Verlag New York, Inc., NY, USA.

Uflacker, R., "Interventional Therapy for Pulmonary Embolism", *Journal of Vascular and Interventional Radiology* Feb. 2001: 12:147-164, Medical University of South Carolina, Charleston, SC, USA.

Müller-Hülsbeck, S. et al. "Mechanical Thrombectomy of Major and Massive Pulmonary Embolism with Use of the Amplatz Thrombectomy Device", *Investigative Radiology* Jun. 2001:36:6:317-322, Department of Radiology, Christian Albrects University, Kiel, Germany.

Schmitz-Rode, T. et al., "Massive Pulmonary Embolism: Percutaneous Embergency Treatment by Pictail Rotation Catheter", *JACC Journal of the American College of Cardiology*, Aug. 2000:36:2:375-380, Elsevier Science, Inc., New York NY, USA.

Schmitz-Rode et al., "Temporary Pulmonary Stent Placement as Emergency Treatment of Pulmonary Embolism," Journal of the American College of Cardiology, vol. 48, No. 4 , 2006 (5 pgs.).

Gibbs, et al., "Temporary Stent as a bail-out device during percutaneous transluminal coronay angioplasty: preliminary clinical experience," British Heart Journal, 1994, 71:372-377, Oct. 12, 1993 (6 pgs.).

Truong et al., "Mechanical Thrombectomy of Iliocaval Thrombosis Using a Protective Expandable Sheath," Cardiovasc Intervent Radiol 27-254-258 (2004) 5 pgs.

Schmitz-Rode et al., "New Mesh Basket for Percutaneous Removal of Wall-Adherent Thrombi in Dialysis Shunts," Cardiovasc Intervent Radiol 16:7-10 (1993) 4 pgs.

METHODS AND APPARATUS FOR TREATING EMBOLISM

RELATED APPLICATIONS

This application claims priority to U.S. Provisional Application Ser. No. 61/728,775 filed Nov. 20, 2012 entitled Devices and Methods for Treatment of Vascular Occlusion and U.S. Provisional Application Ser. No. 61/750,277 filed Jan. 8, 2013 entitled Devices and Methods for Treatment of Vascular Occlusion, both of which are hereby incorporated herein by reference in their entireties.

FIELD OF THE INVENTION

This invention relates to the apparatus and methods of endovascular treatment of blood clots obstructing passageways in the circulatory system and particularly the endovascular treatment of pulmonary embolism.

BACKGROUND OF THE INVENTION

Thromboembolism is the formation in a blood vessel of a dot (thrombus) that breaks loose (embolizes) and is carried by the blood stream to another location in the circulatory system resulting in a clot or obstruction at that new location. For example, a clot may embolize and plug a vessel in the lungs (pulmonary embolism), the brain (stroke), the gastrointestinal tract, the kidneys, or the legs. Thromboembolism is a significant cause of morbidity (disease) and mortality (death), especially in adults. A thromboembolism can be sudden and massive or it may be small and multiple. A thromboembolism can be any size and a thromboembolic event can happen at any time.

When a thrombus forms in the venous circulation of the body it often embolizes to the lungs. Such a thrombus typically embolizes from the veins of the legs, pelvis, or inferior vena cava and travels to the right heart cavities and then into the pulmonary arteries thus resulting in a pulmonary embolism.

A pulmonary embolism results in right heart failure and decreased blood flow through the lungs with subsequent decreased oxygenation of the lungs, heart and the rest of the body. More specifically, when such a thrombus enters the pulmonary arteries, obstruction and spasm of the different arteries of the lung occurs which further decreases blood flow and gaseous exchange through the lung tissue resulting in pulmonary edema. All of these factors decrease the oxygen in the blood in the left heart. As a result, the oxygenated blood supplied by the coronary arteries to the musculature of both the left and right heart is insufficient for proper contractions of the muscle which further decreases the entire oxygenated blood flow to the rest of the body. This often leads to heart dysfunction and specifically right ventricle dysfunction.

This condition is relatively common and has many causes. Some of the more common causes are prolonged inactivity such as bed rest, extended sitting (e.g., lengthy aircraft travel), dehydration, extensive surgery or protracted disease. Almost all of these causes are characterized by the blood of the inferior peripheral major circulatory system coagulating to varying degrees and resulting in permanent drainage problems.

There exist a number of approaches to treating thromboembolism and particularly pulmonary embolism. Some of those approaches include the use of anticoagulants, thrombolytics and endovascular attempts at removal of the emboli from the pulmonary artery. The endovascular attempts often rely on catheterization of the affected vessels and application of chemical or mechanical agents or both to disintegrate the clot. Invasive surgical intervention in which the emboli is removed by accessing the chest cavity, opening the embolized pulmonary artery and/or its branches and removing the clot is also possible.

The prior approaches to treatment, however, are lacking. For example, the use of agents such as anticoagulants and/or thrombolytics to reduce or remove a pulmonary embolism typically takes a prolonged period of time, e.g., hours and even days, before the treatment is effective. Moreover, such agents can cause hemorrhage in a patient.

And the known mechanical devices for removing an embolism are typically highly complex and prone to cause undue trauma to the vessel. Moreover, such known devices are difficult and expensive to manufacture.

Lastly, the known treatment methods do not emphasize sufficiently the goal of urgently restoring blood flow through the thrombus once the thrombus has been identified. In other words, the known methods focus primarily and firstly on overall clot reduction and removal instead of first focusing on relief of the acute blockage condition followed then by the goal of clot reduction and removal. Hence, known methods are not providing optimal patient care, particularly as such care relates to treatment of a pulmonary embolism.

OBJECTS AND SUMMARY OF THE INVENTION

In view of the foregoing it is an object of the present invention to provide a method and system that initially restores an acceptable level of oxygenated blood to the patient's circulatory system followed by safe and effective removal of the thrombus.

It is a further object of the present invention to treat pulmonary embolism in a minimally invasive manner.

It is a further object of the present invention to provide a system that does not cause undue trauma to the vessel.

BRIEF DESCRIPTION OF THE DRAWINGS

These and other objects, aspects, features and advantages of which the invention is capable will be apparent from the following description of embodiments of the present invention, reference being made to the accompanying drawings, in which.

DESCRIPTION OF EMBODIMENTS

Figure 1A:
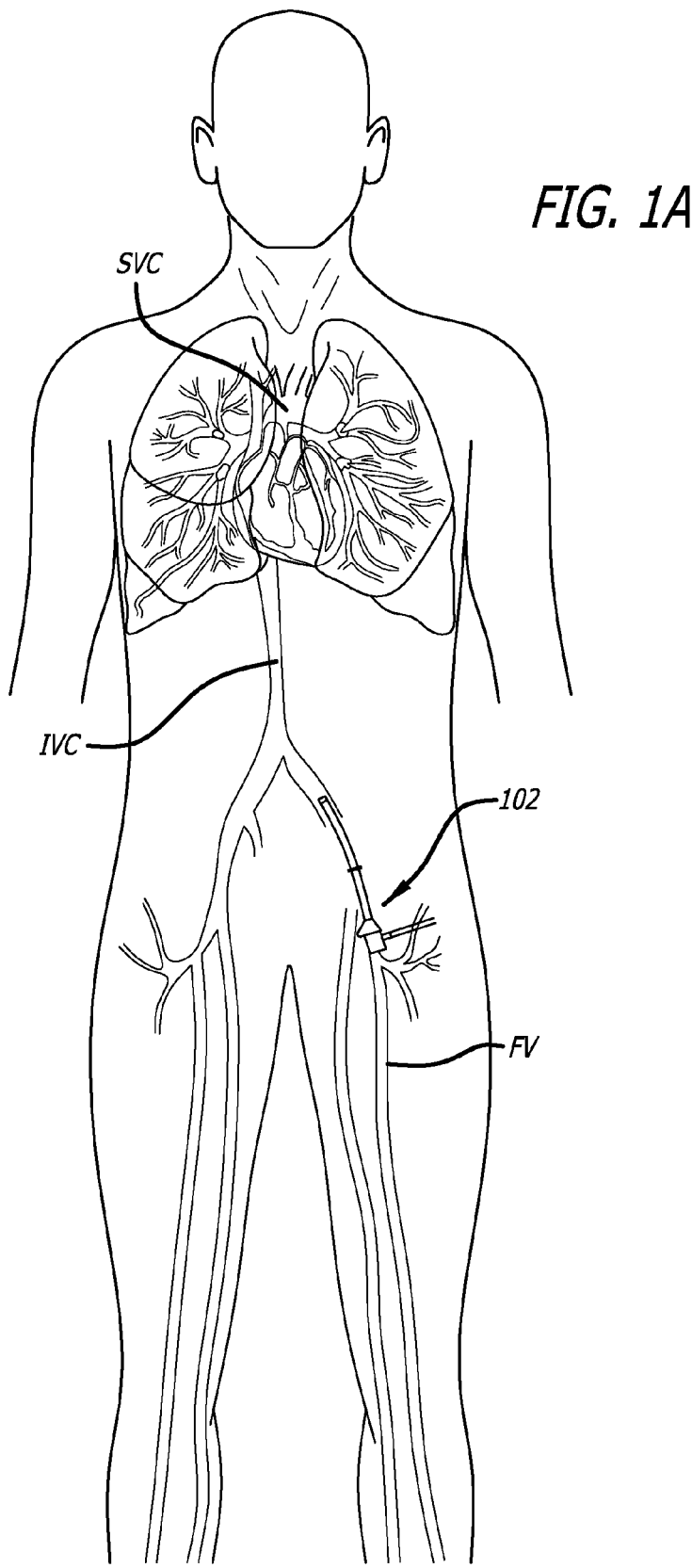
FIG. 1A is a schematic view of a patient with a pulmonary embolism.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1B:
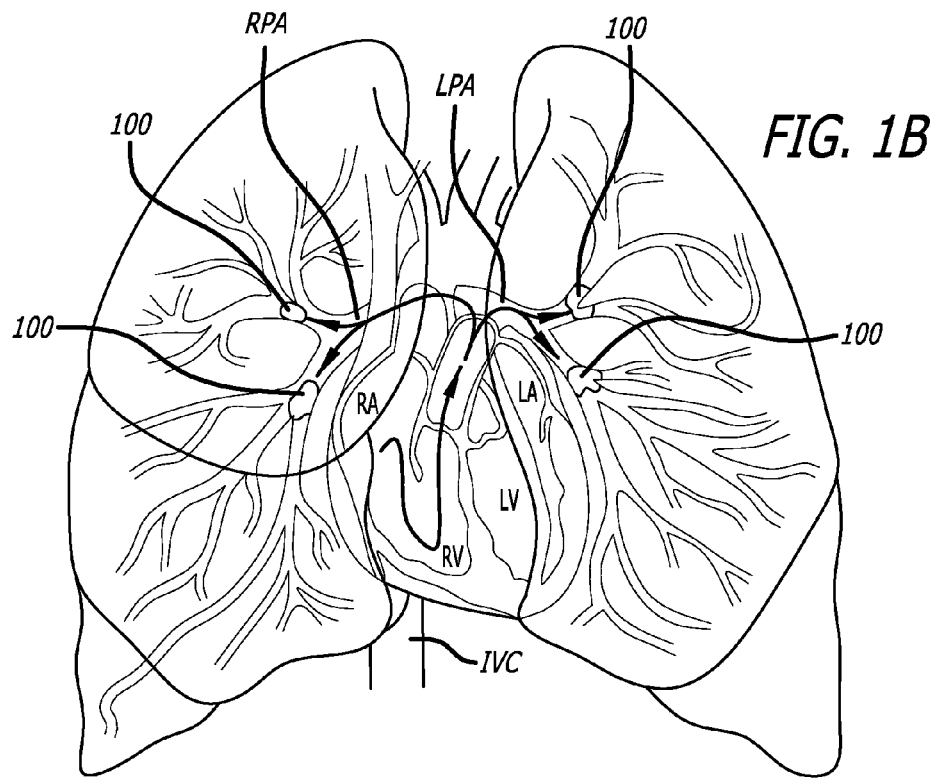
FIG. 1B is an enlarged view of the lung area of the patient depicted in FIG. 1A.
Figure 1C:
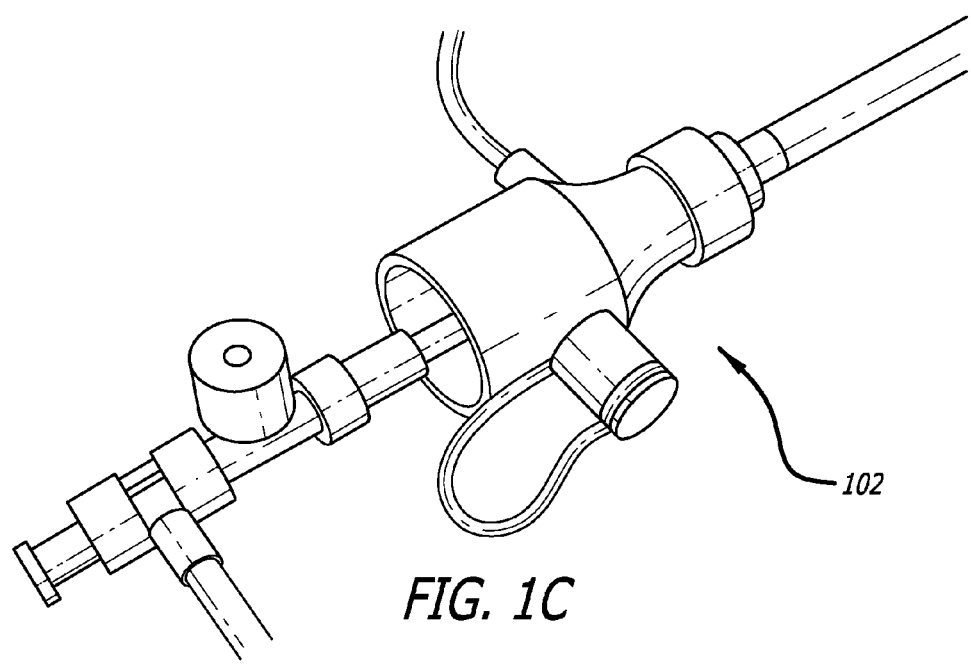
FIG. 1C is an enlarged view of the introducer device depicted being used in the femoral vein of the patient in FIG. 1A.

Referring to FIGS. 1A-1C, these drawings show the typical locations in a human patient where pulmonary embolisms 100 occur in the pulmonary arteries and further discloses the pathway through which access to such pulmonary embolisms 100 is achieved. In particular, an introducer device (e.g., a hemostatic valve) 102 which supports relatively large diameter devices is inserted into the patient into the femoral vein FV in the pelvic area of the patient. The tools and devices needed to treat the pulmonary embolism are then inserted through the introducer 102 into the femoral vein FV through the inferior vena cava IVC to the patient's heart.

It will be understood, however, that other access locations into the venous circulatory system of a patient are possible and which are consistent with the present invention. For example, the user can gain access through the jugular vein, the subclavian vein, the brachial vein or any other vein that connects or eventually leads to the superior vena cava. Use of other vessels that are closer to right atrium RA of the patient's heart may be attractive as this will reduce the length of the instruments needed to reach the pulmonary embolism.

Figure 2:
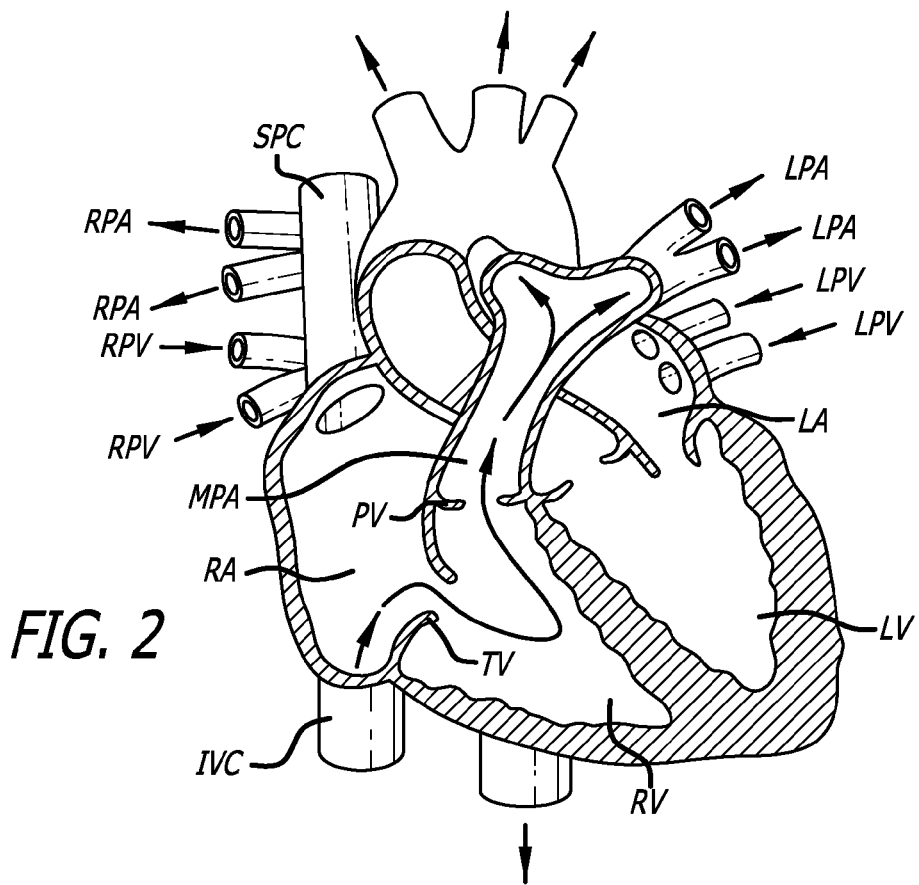
FIG. 2 is a cross-sectional view of a patient's heart.
Figure 3:
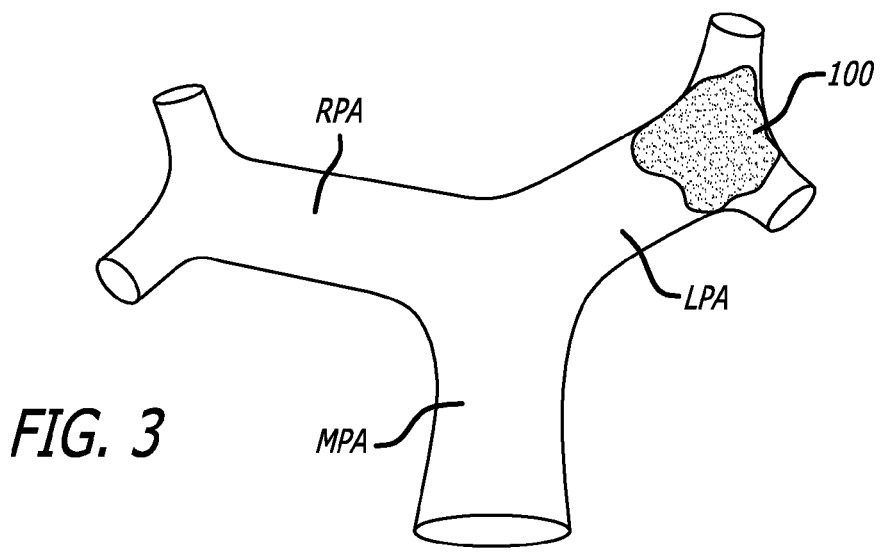
FIG. 3 is a perspective view of a patients main pulmonary artery and right and left pulmonary arteries with a clot located in the left pulmonary artery.

Referring to FIGS. 2 and 3, the tools/devices are then guided through the right atrium RA through the triscupid valve TV, into the right ventricle RV, through the pulmonary valve PV into the main pulmonary artery (MPA). Depending on the location of the embolism 100, the tools/devices are then guided to one or more of the branches of the right pulmonary artery RPA or the left pulmonary artery LPA, including deeper branches thereof, to the location of the pulmonary embolism 100.

Figure 4:
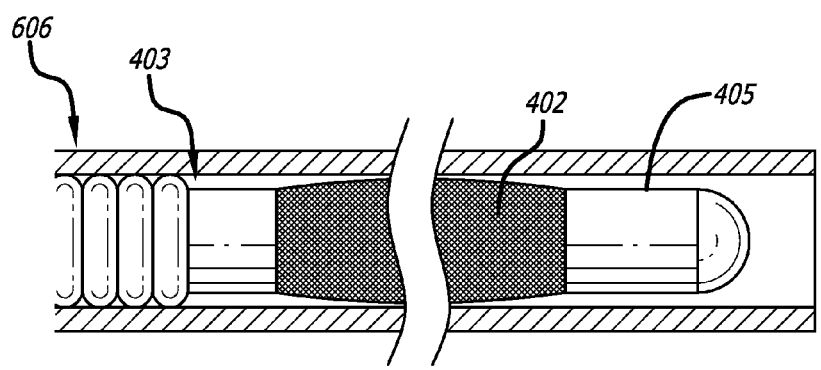
FIG. 4 is a cross-sectional view of a preferred embodiment of a clot treatment device in accordance with the present invention in a compressed, undeployed state.

Referring to FIG. 4, an embodiment of a clot treatment device 402 for restoring blood flow through the clot 100 and for removing at least a portion of the clot is depicted in its undeployed, or compressed state. The device 402 is constrained by a delivery catheter 606. In a preferred embodiment, the device 402 is constituted by a braided material, the ends of which are captured distally by a blunt tip 405 and proximally by an attachment member 403 that connects to a pusher wire 401.

In alternative preferred embodiments, the clot treatment device 402 may be an "over the wire" device, in which case, the pusher wire 401, the attachment member 403 and the blunt tip 405 will have a hollow central lumen for receiving a guide wire.

In yet a further preferred embodiment, the distal end of the clot treatment device shall have a flexible, atraumatic extension from the device.

In preferred embodiments the clot treatment device 402 of the present invention has a generally cylindrical shape that, during use, provides a flow lumen for blood across a clot. The treatment device 402 is not, however, limited to a generally cylindrical shape. For example, the shape can be generally conical, generally concave or generally convex along its axis, so long as such shapes provide the aforesaid lumen for blood flow.

In other preferred embodiments, the treatment device 402 also has a series of radially extending portions 406 which are separated by generally cylindrical portions 412. It is important that the clot treatment device be porous so as to allow the flow of blood therethrough. In this regard, in a preferred embodiment the clot treatment device is made from a mesh or braided material. The material can be a superelastic material such as nitinol or an alternative material such as cobalt chrome alloy. The device can be made from a wire lattice, wire braid or stent. Specific preferred embodiments are discussed throughout this specification.

Figure 5:
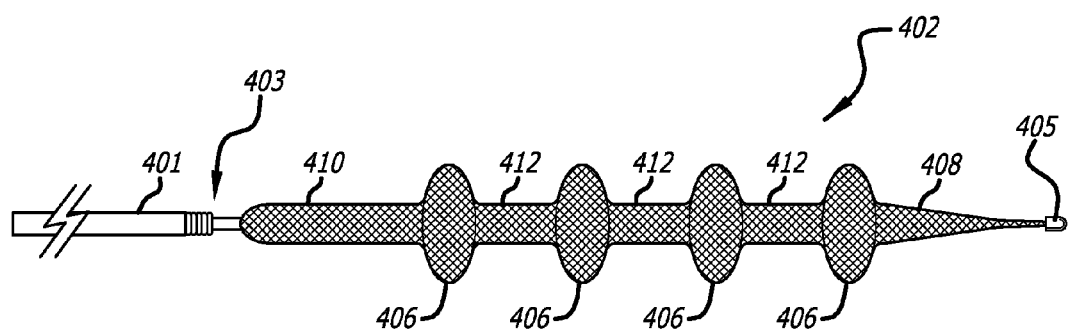
FIG. 5 is a top view of a preferred embodiment of a clot treatment device in accordance with the present invention.

Referring to FIG. 5, the deployed state of the clot treatment device 402 of FIG. 4 is depicted. This preferred embodiment of the clot treatment device 402 is constituted by a mesh structure that is generally cylindrical with a series of radially extending portions 406 situated along the axis of the device 402 and separated by a corresponding series of cylindrical sections 412. Optionally, the generally cylindrical section may have individually have tapers or collectively form a conical lumen (not shown). Each of these radially extending portions 406 is in the shape of a disk. The clot treatment device 402 is self expanding.

Referring to FIGS. 1-3 and 6A-6F, a preferred method of causing flow restoration and clot removal/retrieval with the clot treatment device 402 in a body lumen L is described.

Figure 6A:
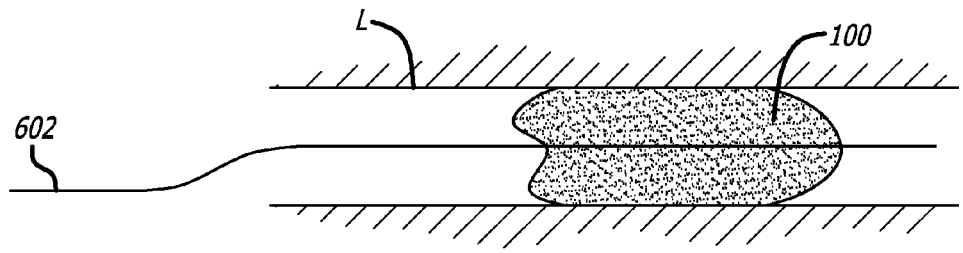
FIGS. 6A-6F are a series of cross-sectional views of a preferred embodiment of the method and device of the present invention.
Figure 6B:
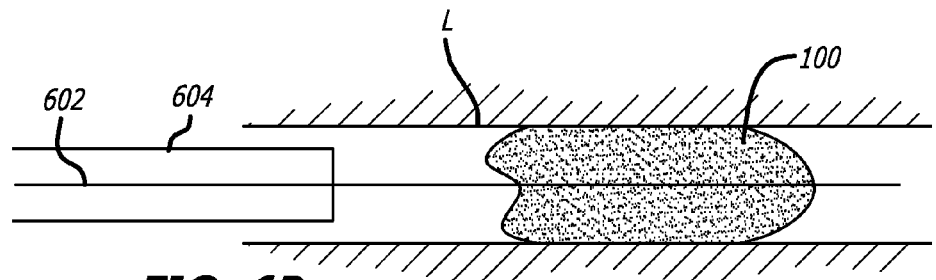

After accessing the femoral vein and inserting a introducer device 102 into the patient, a guide wire 602 is inserted into the patient and maneuvered through the femoral vein FV into the inferior vena cava IVC to the heart. As stated above access can also be achieved through one of the veins leading to the superior vena cava SVC. The guide wire 602 is then urged through the right atrium RA, through the tricuspid valve TV, through the right ventricle RV, through the pulmonary valve PV to the main pulmonary artery MPA and then to a location of the embolism/clot 100 in one of the branches or lumens L of either the right or left pulmonary artery RPA, LPA. In a preferred embodiment, the guide wire 602 is extended through the clot in the body lumen L as shown in FIG. 6A Referring to FIG. 6B, a guide catheter 604 is placed over the guide wire 602 and moved to a location where a distal end of the guide catheter 604 is positioned proximal to the clot 100.

Figure 6C:
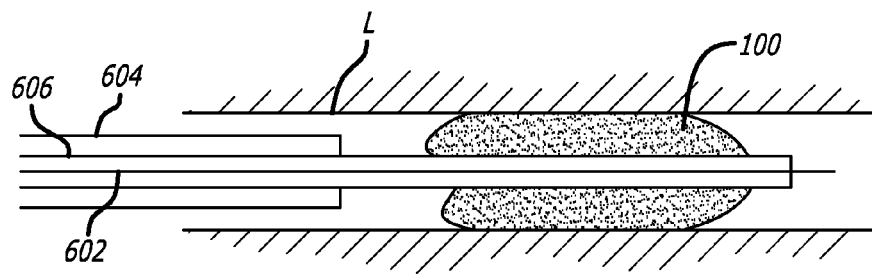

At this point, the guide wire can optionally be withdrawn. However, in a preferred embodiment the guide wire 602 remains and a delivery catheter 606 that is then moved through the guide catheter 604 over the guide wire 602 and is pushed through the clot 100. This is shown in FIG. 6C.

Figure 6D:
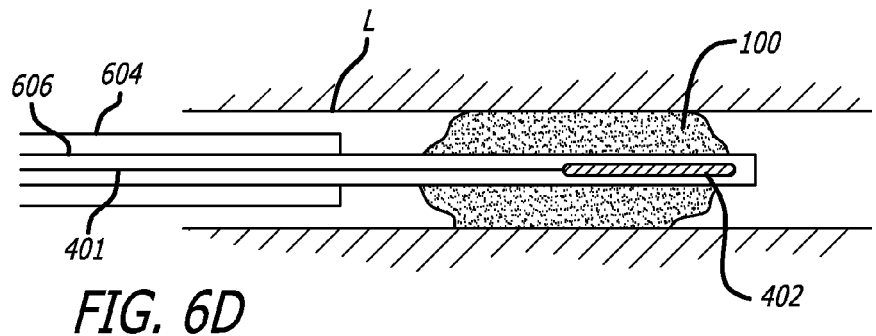

Referring to FIG. 6D, the guide wire 602 is then withdrawn and the clot treatment device 402 in its undeployed (i.e., compressed) state is then moved through the delivery catheter until it is disposed at the distal end of the delivery catheter 606.

Figure 6E:
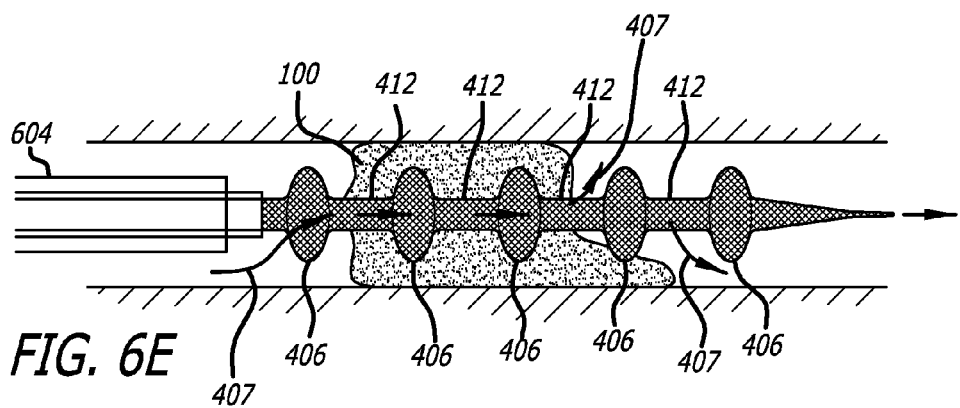

The delivery catheter 606 is then retracted in a proximal direction while maintaining forward pressure on the clot retrieval device 402 via its pusher wire 401 so that the clot treatment device 402 becomes exposed and released from its delivery catheter 606. The clot treatment device 402 radially expands into the clot 100 and in one preferred embodiment, at least a portion of the clot treatment device 402 expands distal of the clot 100. As shown in FIG. 6E, at least one of the radially extending portions 406 of the clot treatment device 402 are located distal to the clot 100 upon expansion of the clot treatment device 402.

It can be seen that upon expansion of the clot treatment device 402 as just described, blood flowthrough the clot 100 is restored. This is depicted with arrows 407 in FIG. 6E. More specifically, the blood is now free to move through the mesh of the clot treatment device 402 and exit the clot treatment device 402 distal to the clot 100. As a result, the acute condition of blockage is corrected thus immediately improving the circulation of oxygenated blood in the patient.

The restoration of blood flow is anticipated to equate with restoration of a substantial portion of the normal blood flow rate for the patient. In less severe. i.e., "sub massive," pulmonary embolism patients, the clot treatment device 402 may increase blood flow rate by at least about 50 ml/min, at least about 150 ml/min or between about 100 to 250 ml/min. In severe, i.e., "massive," pulmonary embolism patients, a larger amount of the pulmonary artery flow is compromised. Hence, in some embodiments, at least about 500 ml/min of blood flow rate may be restored. Moreover, at least a portion of the flow restoration is expected to occur prior to the removal of the clot 100, or any portion thereof.

The restoration of blood flow by the clot treatment device 402 can be achieved in a low pressure environment. For example, the pressure in the target vessel can be less than 60 mmHg and the blood can be venous blood, substantially non-oxygenated blood or low oxygenated blood In addition to restoring blood flow, the expansion of the clot treatment device 402 also impinges or cuts into the clot material. This enhances the subsequent removal of the clot 100 since portions of the clot 100 collect (1) between the radially extending portions 406; (2) through the pores of the mesh forming the radially extending portions 406; (3) along the longitudinal cylindrical sections 412 between the radially extending portions 406 of the removal device 402; and (4) within the clot treatment device 402 itself.

As can be understood from the above description and the drawing figures, the deployment of the clot treatment device 402 results in an outwardly expanding generally cylindrical force being urged against an inner surface of the clot 100. This force pushes the clot material outwardly and creates a lumen through which blood flow is restored. As can also be appreciated, the presence of the radially extending portions 406 on the clot treatment device 402 causes the outwardly expanding generally cylindrical force to vary in magnitude along the axis of the clot treatment device 402. The force on the clot material may be greater at the locations of the radially extending portions 406

In braided embodiments of the clot treatment device 402, deployment, i.e., expansion, of the device leads the filaments of the braid to change their angular orientation with respect to the axis of the device. This angular change may improve or enhances adherence of clot material to the clot treatment device 402.

Figure 6F:
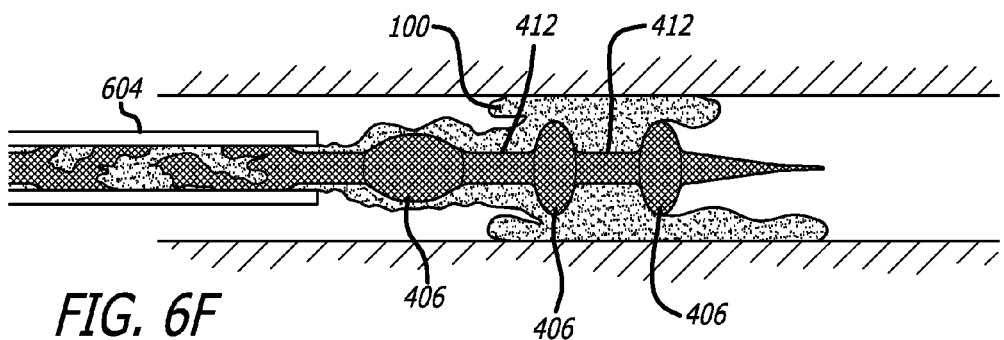

After the clot treatment device 402 has been expanded and blood flow restored, the user then retracts the clot treatment device 402 in a proximal direction as shown in FIG. 6F. In one embodiment, the clot treatment device 402 and the delivery catheter 606 are pulled back simultaneously into the guide catheter 604. This is followed by the entire apparatus (i.e., clot treatment device 402, delivery catheter 606 and guide catheter 604) being withdrawn through the heart and the venous circulation and out from the body.

As further shown in FIG. 6F, the clot treatment device 402 may become elongated as it is being withdrawn into the guide catheter 604 due to the resistance it encounters from the presence of clot material of the clot 100. The presence of the radially extending portions 406 may allow elongation that enhances the capability of the device 402 to capture the maximum amount of clot material. This is further discussed below with respect to the surface area and expansion ratio of preferred embodiments of the clot treatment device 402.

It will be appreciated that variations in the above-described method are contemplated. For example, in certain circumstances a guide catheter 604 may not be necessary or desirable and the user may chose to use only the delivery catheter 606 for placing and manipulation of the clot treatment device 402. As a further example, the clot may be of such a nature that the user may desire repeat the above-described process, or at least portions of it, in order to more fully remove the clot 100 or clot material.

Figure 7A:
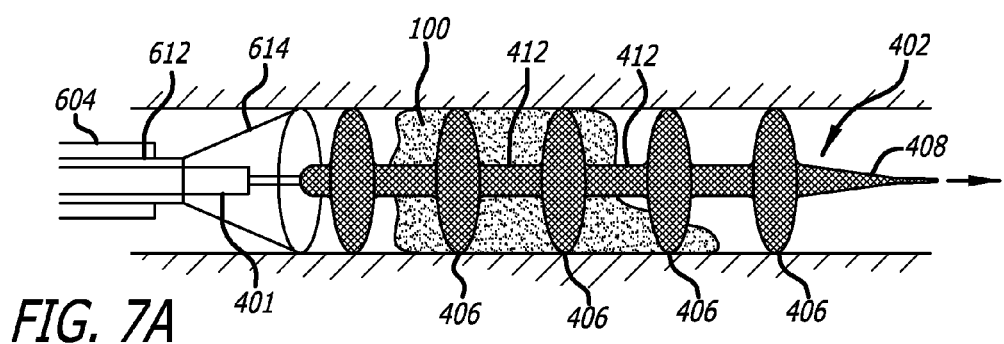
FIGS. 7A-7B are a series of cross-sectional views of a preferred embodiment of the method and device of the present invention.
Figure 7B:
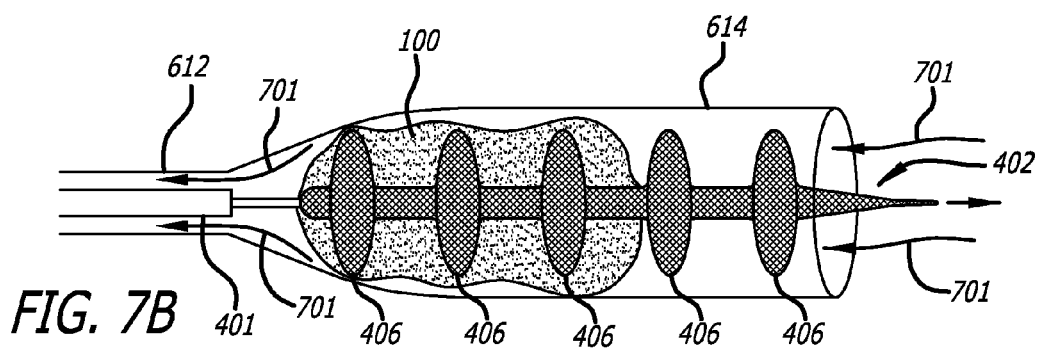

Referring next to FIGS. 7A-7B, it may be advantageous to include the use of a collection or funnel catheter 612 to assist in the removal of the clot 100. Such a funnel catheter 612 has an expandable portion 614 at its distal end and may be situated between the guide catheter 604 and the delivery catheter 608 or may be part of the guide catheter 604. In the presence of the collection catheter 612, the clot treatment device 402 is pulled proximally into the collection catheter 612 such that the clot or portions of it are captured within the collection catheter 612. In an alternative embodiment, the collection catheter 612 can be pushed distally over the clot treatment device 402 and capture the clot, or portions thereof, in that manner. If the collection catheter 612 is separate from the guide catheter 606, the collection catheter with the clot treatment device 402 is then pulled into the guide catheter for ultimate removal of all devices (and the clot) from the patient.

In certain circumstances, it may be advisable to remove the clot 100 without capturing it in the guide catheter 606 or the collection catheter 612 (if used) and remove the clot 100 by withdrawing the entire system, e.g., guide catheter 605, delivery catheter 604, clot treatment device 402 and collection catheter 612 (if used) simultaneously.

In a preferred embodiment the collection catheter 612 is constructed as a mesh or braid or stent structure. Such structure assists in retrieving and containing the clot material in the withdrawal process. In yet further preferred embodiments, the collection catheter 612 contains structural features to assist in the expansion of the funnel portion 614 and to hold the funnel portion 614 open towards the wall of the blood vessel. Such features (not shown) include interwoven support struts, self expanding material (e.g., nitinol), longitudinal wire supports, stent supports, polymeric webbing, etc.

Figure 8:
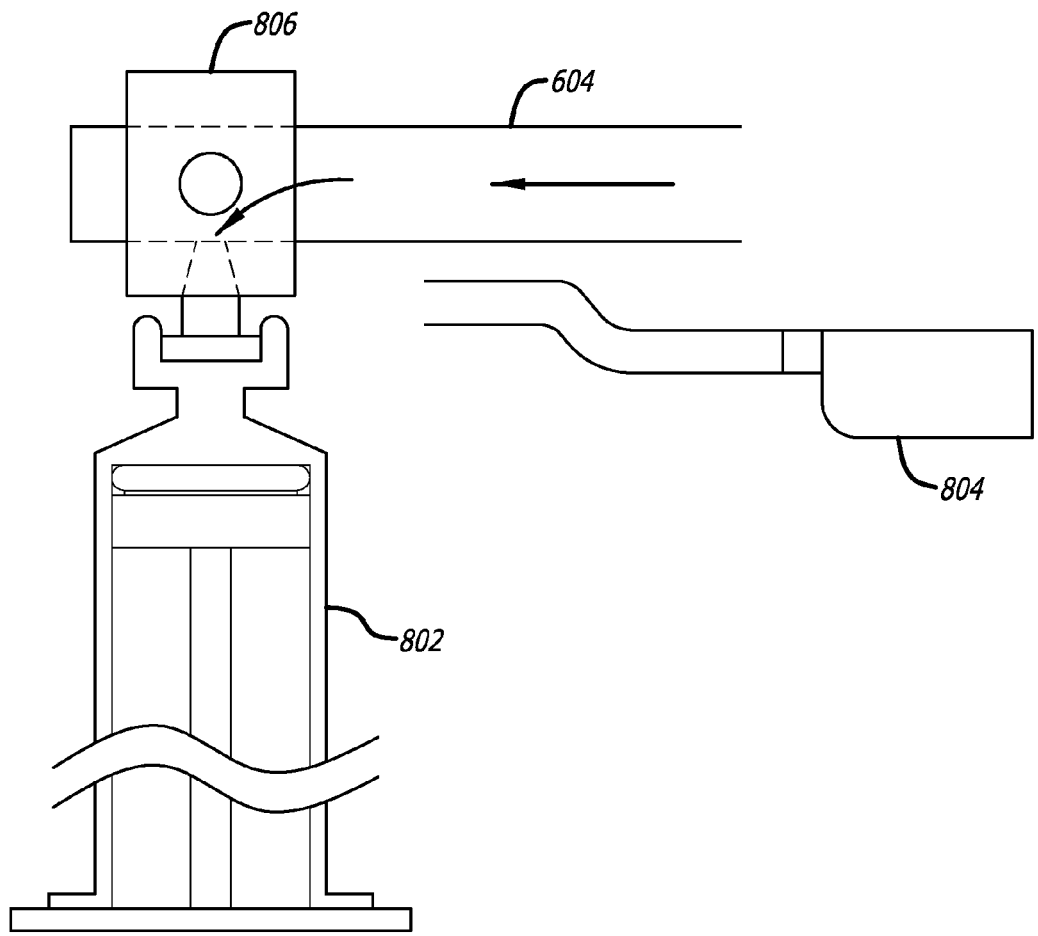
FIG. 8 is a cross-sectional view of another preferred embodiment of the method and device of the present invention; and, FIGS. 9A-9H show cross-sectional views of preferred embodiments of a clot treatment device in accordance with the present invention.

In another embodiment of the present invention, a vacuum apparatus may be used to aid in the removal of the clot material. Referring to FIG. 8, a syringe 802 is shown connected to a vacuum manifold 806 that is in fluid communication with the proximal end of the guide catheter 604. At the time the clot treatment device 402 (and clot material) is being withdrawn into the guide catheter 604 (or the collection catheter 612), vacuum is applied by pulling on the syringe. Alternative sources of vacuum 804 are also acceptable, e.g., a vacuum pump. A system is also contemplated whereby vacuum is actuated automatically when the clot treatment device 402 (and the clot material) is being withdrawn. A representation of the effect of the use of vacuum can be seen with reference to FIG. 7B which shows how vacuum causes flow 701 into the catheter 612.

Referring now to FIGS. 9A-9H, alternative preferred embodiments of the clot treatment device 402 are disclosed.

Figure 9A:
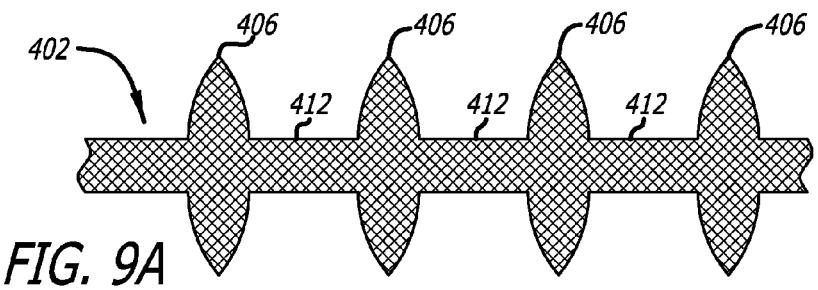

Referring to FIG. 9A, the radially extending portions 406 between the generally cylindrical sections 412 of the clot treatment device 402 are defined by a cylindrical disk shape with a rounded triangular cross-section.

Figure 9B:
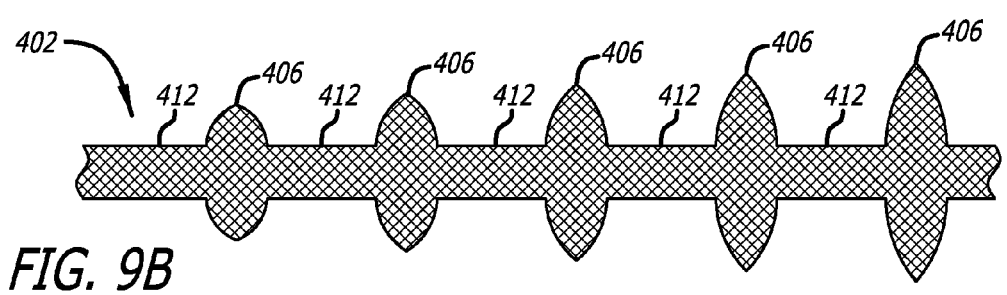

Referring to FIG. 9B, the radially extending portions 406 between the generally cylindrical sections 412 of the clot treatment device 402 are defined by a cylindrical disk shape with a rounded triangular cross-section wherein the diameter of the disk increases along the length of the device 402 thus forming a conical exterior extent.

Figure 9C:
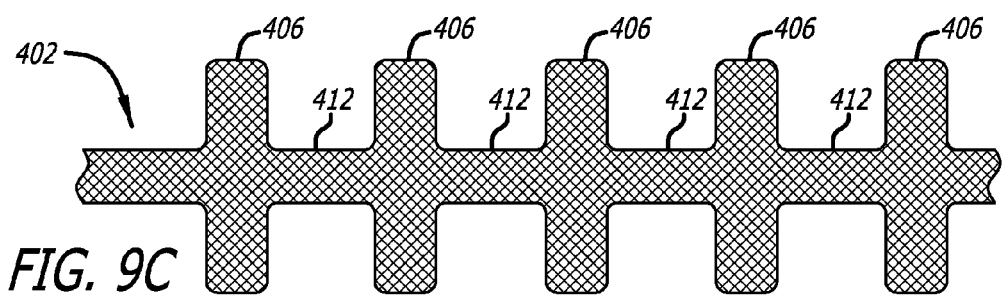

Referring to FIG. 9C, the radially extending portions 406 between the generally cylindrical sections 412 of the clot treatment device 402 are defined by a cylindrical disk shape with a rectangular cross-section.

Figure 9D:
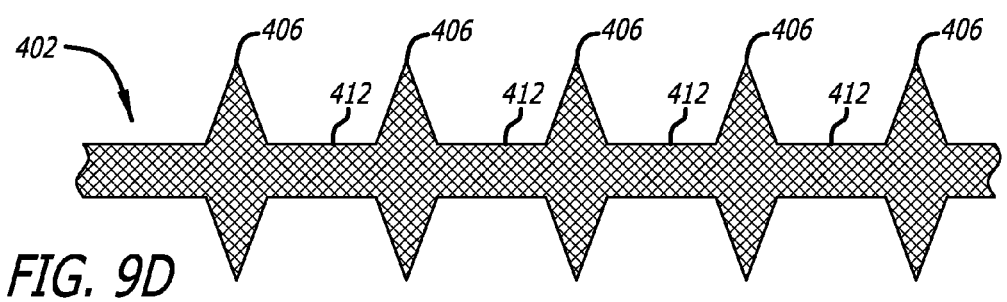

Referring to FIG. 9D, the radially extending portions 406 between the generally cylindrical sections 412 of the clot treatment device 402 are defined by a cylindrical disk shape with a linear (non-rounded) triangular cross-section.

Figure 9E:
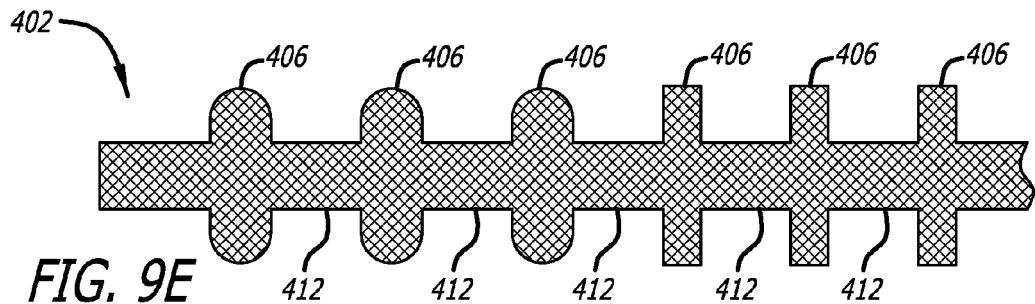

Referring to FIG. 9E, some of the radially extending portions 406 between the generally cylindrical sections 412 of the clot treatment device 402 are defined by a cylindrical disk shape with a rounded cross-section and others have a rectangular cross section.

Figure 9F:
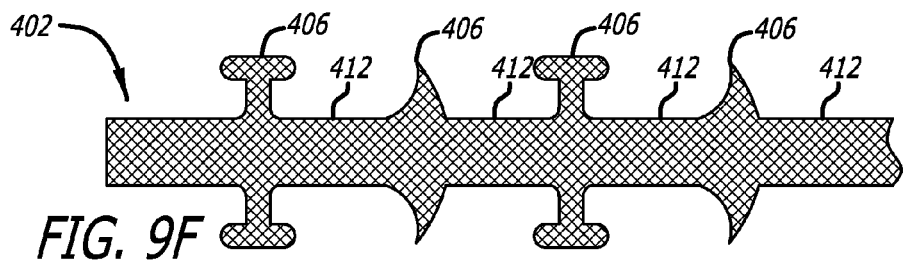

Referring to FIG. 9F, the radially extending portions 406 between the generally cylindrical sections 412 of the clot treatment device 402 alternate between cylindrical disk shape with a T-shaped cross-section and a flare-shaped cross-section.

Figure 9G:
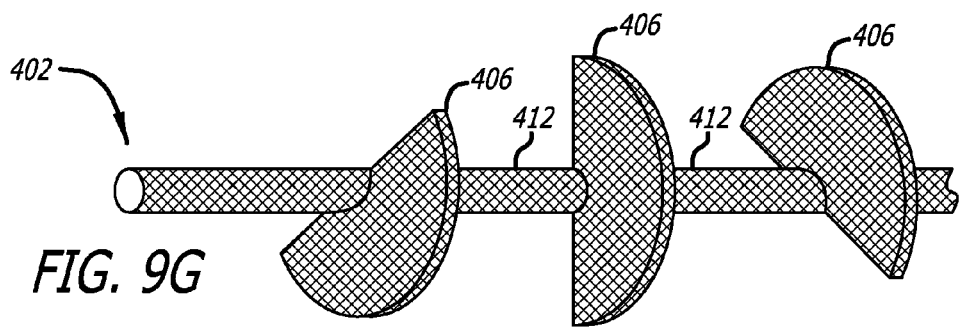

Referring to FIG. 9G, the radially extending portions 406 between the generally cylindrical sections 412 of the clot treatment device 402 are defined by a partial cylindrical disk shapes.

Figure 9H:
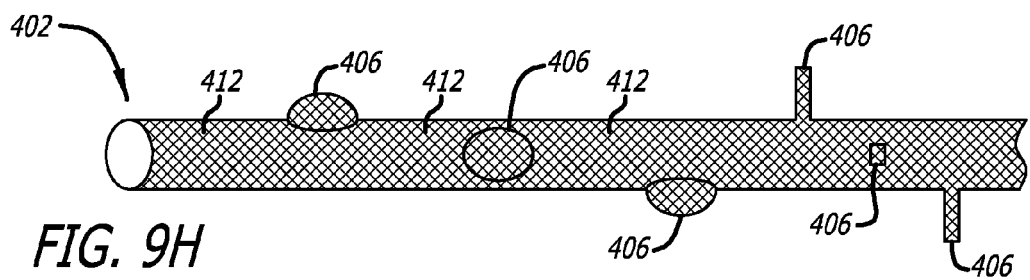

Referring to FIG. 9H, the radially extending portions 406 between the generally cylindrical sections 412 of the clot treatment device 402 are defined by tabs and bumps or protuberances arising from the cylindrical surface of the device 402.

In this regard, it is noted that the radially extending portions 406 provide greater surface area along the device than a device that is uniformly cylindrical. Such increased surface area facilitates the treatment and/or retrieval of a much larger portion of the clot 100 than is generally feasible with a uniformly cylindrical device. For example, in a preferred embodiment of the clot treatment device 402, the device will have an external surface area between 1.5× and 6× the surface area of a uniformly cylindrical device of the same general diameter of the cylindrical sections 412. In other preferred embodiments the ration will be 2× to 4×.

This is advantageous particularly during retraction of the clot treatment device 402 through the clot 100. As shown in FIG. 6F, the clot treatment device 402 may become elongated as it is being withdrawn through the clot 100. Such elongation causes the clot material to encounter greater surface area of the clot treatment device 402 than would otherwise occur with a device that was only generally cylindrical, i.e., that did not incorporate radially extending portions 406. Accordingly the clot treatment device 402 is particularly adept at capturing the maximum amount of clot material during withdrawal.

The clot treatment device 402 is intended for use in large vessels, i.e., vessels with a diameter greater than 8 mm. For example, the diameter of the pulmonary arteries typically range from 15 to 30 mm whereas the first branches of the pulmonary arteries typically range from 10 to 15 mm and the secondary and tertiary branches typically range from 5 to 10 mm. At the same time, however, it is important to minimize the size of catheter providing access to the clot 100. Accordingly, the clot treatment device 402 has a large expansion ratio. In a preferred embodiment the expansion ratio from the diameter of the cylindrical sections 412 in the collapsed state to the expanded state will be between 4 and 8. In another preferred embodiment the ratio will be between 5 and 7. The large expansion ratio also enables the formation of a flow channel in the clot 100 that is large, e.g., on the order of 4-8 mm.

The radially extending portions 406, in their fully expanded position are intended to have a size that matches the diameter of the target blood vessel. However, the diameters may be slightly larger than the vessel diameter so to apply greater radial force against the blood vessel (without causing trauma) in those circumstances when it is desirable to improve clot collection. Similarly, in those circumstances where there is a concern of creating trauma on delicate blood vessels, the radially extending portions 406 may have a diameter that is smaller than the vessel diameter. It is contemplated that different sizes of the device 402 will be available for selection by the user for a particular presentation of the patient.

As for the length of the clot treatment device 402, it is known that a typical pulmonary embolism will have a length within the range between about 2 cm and 10 cm and sometimes between about 1 cm and 20 cm. Accordingly, in a preferred embodiment, the clot treatment device 402 will have a length that exceeds the length of the embolism so that a portion of the clot treatment device is positioned distal of the clot 100 during expansion.

With regard to the delivery catheter 606, in a preferred embodiment for use with a pulmonary embolism, the size will be around 1 F-6 F. Smaller diameters will pass through the clot 100 more easily. In addition, the delivery catheter 606 may have stiffness characteristics to assist in making sure the delivery catheter 606 passes through the clot in a smooth manner. Such stiffness characteristics include self expanding nitinol wire braids or stent structures that are contained within the structure of the delivery catheter 606. The delivery catheter 606 also has sufficient flexibility so that it may carry the clot treatment device 402 and still pass through a tortuous vessel path as described above starting with insertion of the delivery catheter 606 in the femoral vein FV.

In some preferred embodiments, the method and device in accordance with the present invention may reduce the Mean Resting Pulmonary Artery Pressure (MRPAP). Upon at least partial relief from the clot 100, MRPAP may be reduced by about 20-50 mmHg to a normal range of 8-20 mmHg. In some embodiments, the reduction in MRPAP may be about 25-50%. In some embodiments, the reduction in MRPAP may be about 15% to 40% and in other embodiments between about 30% and 75%.

Such a reduction in MRPAP can occur in two steps. The first step is when the clot treatment device 402 is first deployed and blood flow is at least partially restored. The second step is when the clot treatment device 402 is retracted and at least some of the clot 100 is removed from the vessel.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of treating a pulmonary embolism comprising:
delivering an embolectomy device through the heart to a pulmonary embolism that at least partially restricts blood flow through a pulmonary vessel, wherein the embolectomy device comprises an expandable cylindrical section and at least first and second radial expansion members configured to expand outwardly from the cylindrical section, wherein the cylindrical section is between the first and second radial expansion members;
deploying the embolectomy device within the pulmonary embolism so as to restore blood flow through said pulmonary embolism,
wherein deploying the embolectomy device comprises expanding the cylindrical section within the pulmonary embolism such that the cylindrical section forms an expanded flow channel through the pulmonary embolism and expanding the radial expansion member to a greater extent than the cylindrical section, and wherein at full expansion of the cylindrical member the radial expansion member projects outward from the cylindrical member, and wherein the cylindrical section has a first length in a longitudinal direction and each of the first and second radial expansion members have a length in the longitudinal direction that is less than the first length of the cylindrical section at full expansion;
moving the embolectomy device and at least a portion of the pulmonary embolism along the pulmonary vessel; and
withdrawing the embolectomy device and at least a portion of the pulmonary embolism from the pulmonary vessel.

2. A method according to claim 1, wherein deploying the embolectomy device comprises expanding a plurality of radial extensions of said embolectomy device.

3. A method according to claim 2, wherein at least one of said plurality of radial extensions is expanded distal to said pulmonary embolism.

4. A method according to claim 1, wherein said deploying the embolectomy device comprises expanding a plurality of cylindrical portions and a plurality of radial expansion members of said device, and wherein the cylindrical portions are between the radial expansion members.

5. A method according to claim 4, wherein the embolectomy device comprises a continuous mesh and the cylindrical portions and the radial expansion members are integrally formed of the mesh, and expanding the plurality of radial expansion members and the cylindrical portions comprises expanding the mesh to a greater extent at the radial expansion members than at the cylindrical portions.

6. A method according to claim 4, wherein deploying the embolectomy device comprises expanding said device such that a surface area of said embolectomy device expands within a range of at least two times to four times the surface area of a uniformly cylindrical device.

7. A method according to claim 1, wherein deploying the embolectomy device comprises causing filaments of said embolectomy device to change angle with respect to an axis of said device and thereby increase adherence of material of said pulmonary embolism to said embolectomy device.

8. A method according to claim 1, further comprising applying vacuum during said retracting of said embolectomy device.

9. A method according to claim 1, wherein the cylindrical section and the radial expansion member are self-expanding.

10. A method of treating a pulmonary embolism comprising:
accessing a venous vessel of a patient;
inserting a catheter into said venous vessel and urging the catheter through said venous vessel, through chambers of the patient's heart and into a pulmonary artery until a distal end of the catheter is located at a distal end region of a pulmonary embolism of the patient;
delivering a clot treatment device having a flow portion and at least first and second radial expansion members through the catheter and into the pulmonary embolism, wherein the flow portion is between the first and second radial expansion members;
expanding the flow portion from a compressed state to an expanded elongated state such that a diameter of the flow portion increases by a ratio of at least 4:1 to 8:1 and thereby forms a flow channel that restores blood flow through the pulmonary embolism;
expanding the radial expansion member to a greater extent than the diameter of the flow portion in the expanded elongated state, and wherein at full expansion of the flow portion the radial expansion member projects outward from the flow portion, and wherein the flow portion has a first length in a longitudinal direction and each of the first and second radial expansion members have a length in the longitudinal direction that is less than the first length of the flow portion at full expansion;
retracting the clot treatment device and at least a portion of the clot material along the vessel.

11. A method according to claim 10, wherein the device includes a plurality of radial expansion members and the method comprises expanding the plurality of radial expansion members to a greater extent than the flow portion.

12. A method according to claim 11, wherein at least one of said plurality of radial extensions is expanded distal to said pulmonary embolism.

13. A method according to claim 11, wherein expanding the flow portion and the radial expansion member comprises causing filaments of said clot treatment device to change angle with respect to an axis of said device and thereby increase adherence of material of said pulmonary embolism to said clot treatment device.

14. A method according to claim 11, further comprising applying vacuum during said retracting of said expanded clot treatment device.

15. A method according to claim 11, wherein the flow portion and the radial expansion member are self-expanding.

16. A method according to claim 11, wherein said expanding of said embolectomy device comprises expanding said device such that a surface area of said clot treatment device expands within a range of at least two times to four times the surface area of a uniformly cylindrical device.

17. A method according to claim 11, wherein said expanding includes expanding a portion of said clot treatment device distal to said pulmonary embolism.

18. A method according to claim 17, wherein said expanding includes expanding said clot treatment device so that it exceeds the length of said pulmonary embolism.

19. A method according to claim 11, wherein said restoring of said blood flow reduces a mean resting pulmonary artery pressure within a range of about 20-50 mHg.

20. A method of treating a pulmonary embolism comprising:
accessing a venous vessel of a patient;
inserting a delivery catheter containing a clot treatment device into the venous vessel, through the venous circulatory system of the patient, and through the heart to a clot of a pulmonary embolism;

urging the delivery catheter through the clot;

deploying the clot treatment device from the delivery catheter and causing an outwardly expanding radial force along a cylinder to be urged against an inner surface of said clot to form a channel of not less than about 4 mm to 8 mm entirely through said clot and causing at least first and second radial expansion members to expand to a greater extent than the channel, wherein the cylinder is between the first and second radial expansion members, and wherein at full expansion the cylinder has a first length in a longitudinal direction, the first and second radial expansion members project outward from the cylinder, and each the first and second radial expansion members have a length in the longitudinal direction that is less than the first length of the cylinder; and withdrawing said clot treatment device through said clot and thereby removing clot material from said clot.

21. A method according to claim 20, wherein said outwardly expanding radial force comprises generating a force that varies in magnitude along a length of said clot treatment device.

22. A method according to claim 21, wherein said variation in magnitude is a result of a plurality of radial expansion members expanding along an axis of the clot retrieval device.

23. A method according to claim 20, wherein said causing said outwardly expanding radial force is comprised of expanding the cylinder of the clot treatment device in said clot.

24. A method according to claim 21, wherein said generating of a force that varies in magnitude comprises expanding radial expansion members thereon in said clot.

25. A method according to claim 20, wherein withdrawing said clot treatment device includes elongating said clot treatment device as said clot treatment device contacts material of said clot.

26. A method according to claim 20, wherein said deploying of said clot treatment device includes cutting into material of said clot.

27. A method according to claim 20, wherein said deploying of said clot treatment device includes causing filaments of said clot treatment device to change angle with respect to an axis of said device and thereby increase adherence of material of said clot to said clot treatment device.

28. A method according to claim 20, wherein the cylinder and the radial expansion member are self-expanding.

29. A method according to claim 20, further comprising applying vacuum during said withdrawing of said clot treatment device.

30. A method according to claim 20, wherein said deploying of said clot treatment device includes increasing blood flow rate through said clot by at least about 50 ml/min.

* * * * *

UNITED STATES PATENT AND TRADEMARK OFFICE
CERTIFICATE OF CORRECTION

PATENT NO. : 8,784,434 B2  
APPLICATION NO. : 13/843742  
DATED : July 22, 2014  
INVENTOR(S) : Rosenbluth et al.

It is certified that error appears in the above-identified patent and that said Letters Patent is hereby corrected as shown below:

On title page 3, in column 2, item [56] under "Other Publications", line 2, delete "Albrects" and insert -- Albrechts --, therefor.

On title page 3, in column 2, item [56] under "Other Publications", line 5, delete "Embergency" and insert -- Emergency --, therefor.

On title page 3, in column 2, item [56] under "Other Publications", line 12, delete "coronay" and insert -- coronary --, therefor.

In the Specification

Column 1, line 24, delete "dot" and insert -- clot --, therefor.

Column 2, line 57, delete "patients" and insert -- patient's --, therefor.

Column 3, line 46, delete "triscupid" and insert -- tricuspid --, therefor.

Column 4, line 49, delete "6A" and insert -- 6A. --, therefor.

Column 5, line 33, delete "blood" and insert -- blood. --, therefor.

Column 5, line 54, delete "406" and insert -- 406. --, therefor.

Column 6, line 15, delete "chose" and insert -- choose --, therefor.

In the Claims

Column 11, line 15, claim 20, delete "each the" and insert -- each of the --, therefor.

Signed and Sealed this  
Fourteenth Day of October, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,784,434 B2 | Page 1 of 1 |
| APPLICATION NO. | : 13/843742 | |
| DATED | : July 22, 2014 | |
| INVENTOR(S) | : Robert F. Rosenbluth et al. | |

It is certified that error appears in the above-identified patent and that said Letters Patent is hereby corrected as shown below:

On the Title page, in item (73), in column 1, under "Assignee", line 1, delete "Inceptus Medical, Inc.," and insert -- Inceptus Medical, LLC., --, therefor.

Signed and Sealed this
Second Day of June, 2015

Michelle K. Lee
*Director of the United States Patent and Trademark Office*